US006769580B2

(12) United States Patent
Muderlak et al.

(10) Patent No.: US 6,769,580 B2
(45) Date of Patent: Aug. 3, 2004

(54) SYSTEM AND METHOD FOR PROGRAMMABLY DISPENSING MATERIAL

(75) Inventors: Kenneth J. Muderlak, Shorewood, WI (US); Rocky Shieh, Hsin Chu (TW)

(73) Assignee: Technical Concepts, LLC, Mundelein, IL (US)

( * ) Notice: Subject to any disclaimer, the term of this patent is extended or adjusted under 35 U.S.C. 154(b) by 0 days.

(21) Appl. No.: 10/062,262

(22) Filed: Feb. 1, 2002

(65) Prior Publication Data

US 2002/0166871 A1 Nov. 14, 2002

Related U.S. Application Data

(62) Division of application No. 09/661,945, filed on Sep. 14, 2000, now Pat. No. 6,394,310.
(60) Provisional application No. 60/154,101, filed on Sep. 15, 1999, and provisional application No. 60/156,650, filed on Sep. 29, 1999.

(51) Int. Cl.[7] .................................................. B67B 7/00
(52) U.S. Cl. .......................................... 222/646; 222/1
(58) Field of Search .......................... 222/1, 644, 645, 222/646, 649

(56) References Cited

U.S. PATENT DOCUMENTS

| | | | |
|---|---|---|---|
| 5,038,972 A | 8/1991 | Muderlak et al. | |
| RE34,847 E | 2/1995 | Muderlak et al. | |
| 5,449,117 A | 9/1995 | Muderlak et al. | |
| 5,772,074 A | 6/1998 | Dial et al. | |
| 5,823,390 A | 10/1998 | Muderlak et al. | |
| 5,884,808 A | 3/1999 | Muderlak et al. | |
| 5,908,140 A | 6/1999 | Muderlak et al. | |
| 6,394,310 B1 * | 5/2002 | Muderlak et al. | .............. 222/1 |

* cited by examiner

Primary Examiner—Kenneth Bomberg
(74) Attorney, Agent, or Firm—Brinks Hofer Gilson & Lione (57) ABSTRACT

A system and method for dispensing material from a container. The method comprises the steps of receiving a dispensing time, receiving a working interval, receiving a plurality of working days, and dispensing the material from the container during the dispensing time, during the working interval and on one of the plurality of working days.

22 Claims, 7 Drawing Sheets

| Working Hours = 24 | | | |
|---|---|---|---|
| Service Day | 5 Days / Week | 6 Days / Week | 7 Days / Week |
| 30 | 10 min. 17 sec. | 12 min. 21 sec. | 14 min. 24 sec. |
| 60 | 20 min. 34 sec. | 24 min. 41 sec. | 28 min. 48 sec. |
| 90 | 30 min. 51 sec. | 37 min. 2 sec. | 43 min. 12 sec. |

FIG. 4A

| Working Hours = 12 | | | |
|---|---|---|---|
| Service Day | 5 Days / Week | 6 Days / Week | 7 Days / Week |
| 30 | 5 min. 9 sec. | 6 min. 10 sec. | 7 min. 12 sec. |
| 60 | 10 min. 17 sec. | 12 min. 21 sec. | 14 min. 24 sec. |
| 90 | 15 min. 26 sec. | 18 min. 31 sec. | 21 min. 36 sec. |

SYSTEM AND METHOD FOR PROGRAMMABLY DISPENSING MATERIAL

CROSS REFERENCE TO RELATED APPLICATION

This application is a division of U.S. patent application Ser. No. 09/661,945 filed Sep. 14, 2000 now U.S. Pat. No. 6,394,310, which claims the benefit of U.S. Provisional Application No. 60/154,101, filed Sep. 15, 1999 and U.S. Provisional Application No. 60/156,650, filed Sep. 29, 1999, all of which are incorporated herein by reference.

TECHNICAL FIELD

The present invention relates to a system and method for dispensing material. More particularly, the invention relates to a system and method for programmably setting the number of days between refilling a dispensing device.

BACKGROUND OF THE INVENTION

In the past, various solid materials were utilized which sublimated, thereby dispersing, a substitute odor for the odor found in public facilities. In order to enhance the dispersion of such sublimating materials, many suppliers developed powered fan devices which assisted in the dispersal of the sublimated material. Such devices are well known in the art. For example, the common assignee of the present invention owns U.S. Pat. No. 4,830,791 entitled Odor Control Device, issued May 16, 1989, which discloses a solid dispensing device. Also, odor control devices where a pressurized aerosol container is utilized are well known in the art. Aerosol-type dispensing devices typically include a battery-powered motor that actuates the nozzle on the aerosol container on a periodic basis. These conventional dispensing devices have significant disadvantages. For example, these devices do not inform the user of the amount of time or the number of days remaining until the container is replaced or refilled.

SUMMARY OF THE INVENTION

The disadvantages of conventional dispensing apparatuses are substantially overcome with the present invention by providing a novel programmable apparatus for dispensing material, such as odorizing, cleaning, or disinfecting material, which allows a user to program the dispensing device to set the number of days between refills.

In accordance with the present invention, a method is provided for dispensing material from a container. The method comprises the steps of receiving a dispensing time, receiving a working interval, receiving a plurality of working days, and dispensing the material from the container during the dispensing time, during the working interval and on one of the plurality of working days.

In an additional embodiment, a method for dispensing material from a container comprises the steps of receiving a dispensing time, determining a dispensing interval based on the dispensing time, and dispensing the material from the container at a frequency inversely proportional to the dispensing interval. In another embodiment, a method for dispensing material from a container comprises the steps of receiving a dispensing time, receiving a number of working hours/day, determining a number of working days, determining a dispensing interval based on the dispensing time, the number of working hours/day and the number of working days, and dispensing the material from the container at a frequency inversely proportional to the dispensing interval.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood with reference to the following figures The components in the figures are not necessarily to scale, emphasis instead being placed upon illustrating the principals of the invention. Moreover, in the figures, like reference numerals designate corresponding parts throughout the different views.

DETAILED DESCRIPTION OF THE INVENTION

Systems and methods consistent with the present invention provide an improved dispensing apparatus or device which allows a user to select the service day, i.e., the number of days that the dispensing device operates between refills. The method also allows the user to select the working interval, i.e., the number of hours/day that the apparatus dispenses the material, and to select the days of the week that the dispensing device is active. The dispensing apparatus adjusts the dispensing interval, i.e., the interval between dispensing pulses, to ensure that the service day reflects the number of days the dispensing device operates between refills.

Figure 1A:
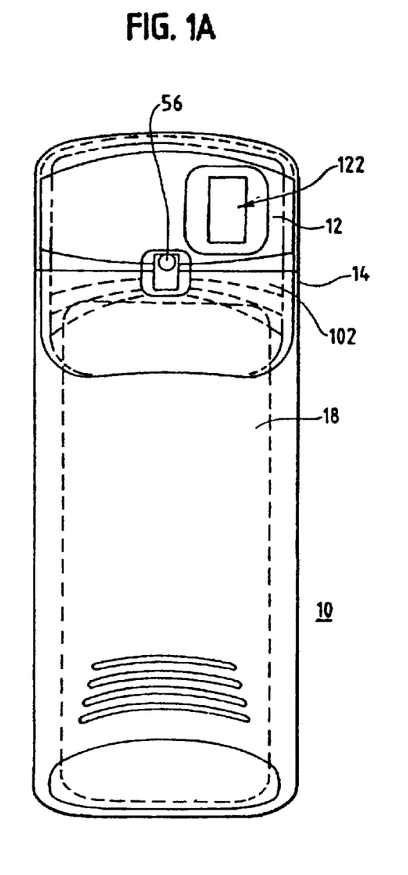
FIG. 1A is a front elevational view of a specific embodiment of a dispensing apparatus, according to the present invention.
Figure 1B:
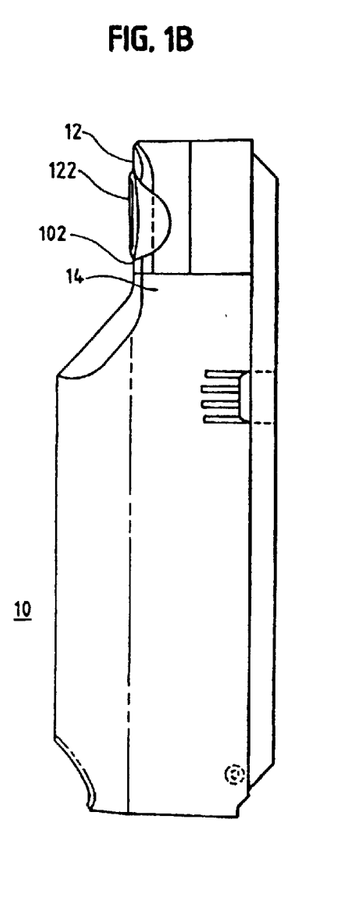
FIG. 1B is a side elevational view of the dispensing apparatus shown in FIG. 1A.

Referring now to FIG. 1A and FIG. 1B, the dispensing device 10 is generally shown. The dispensing device 10 includes a front panel 12 attached to an enclosure 14, or formed integrally with the enclosure. The enclosure 14 may be formed from plastic or other suitable material. A container 18, shown in phantom in FIG. 1A, is housed within the enclosure 14 and in one embodiment may contain an odorizing, cleaning, or disinfecting chemical. The container 18 may be a pressurized aerosol type container where depression of a nozzle 56 attached to the container 18 causes a predetermined amount of chemical to be dispensed. The container 18 may also be a liquid pump type container or any other container where depression of the nozzle 56 dispenses material. The nozzle 56 is actuated by a hammer and cam mechanism (not shown) which is coupled to a motor (not shown) through a gearing mechanism (not shown). The hammer and cam mechanism, the motor, the gearing mechanism, and the mechanics of the dispensing device 10 generally, are described in U.S. Pat. No. 5,038,972 issued on Aug. 13, 1991, entitled Metered Aerosol Fragrance Dispensing Mechanism, reissued on Feb. 7, 1995 as Re. 34,847, both of which are owned by the common assignee of this patent/ patent application and are hereby incorporated by reference herein.

Figure 2:
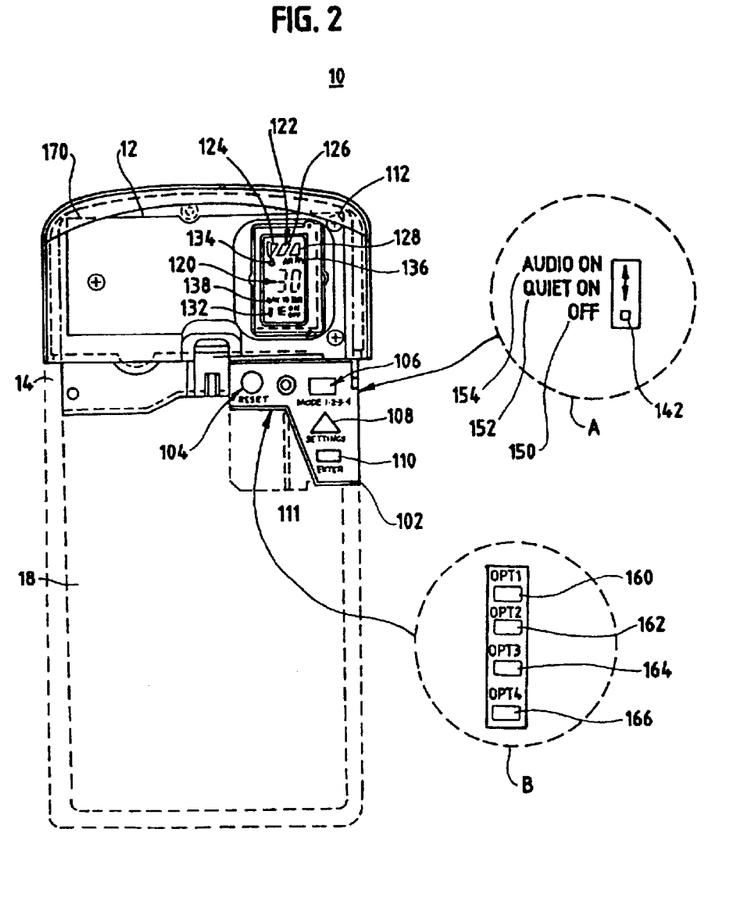
FIG. 2 is a pictorial representation of a portion of a front panel of one embodiment of the dispensing device shown in FIG. 1A, particularly illustrating control switches and an LCD display.

Referring now to FIG. 2, one embodiment of the invention is shown in which a control panel 102 is mounted on the front panel 12 or may be integrally formed with the front panel 12. The control panel 102 includes a reset switch 104, a mode switch 106, a "settings" or "adjust" switch 108, an enter switch 110, a manual on/off rocker-type switch 111, and a liquid crystal display (LCD display) 112 having several separate LCD portions The reset switch 104, the mode switch 106, the settings switch 108, and the enter switch 110 are all pushbutton type momentary contact switches in the illustrated embodiment and may provide multiple functions when depressed multiple times in succession, as will be described in greater detail hereinafter. Of course, the switches described above may be any type of suitable button or switch known in the art.

Figure 3:
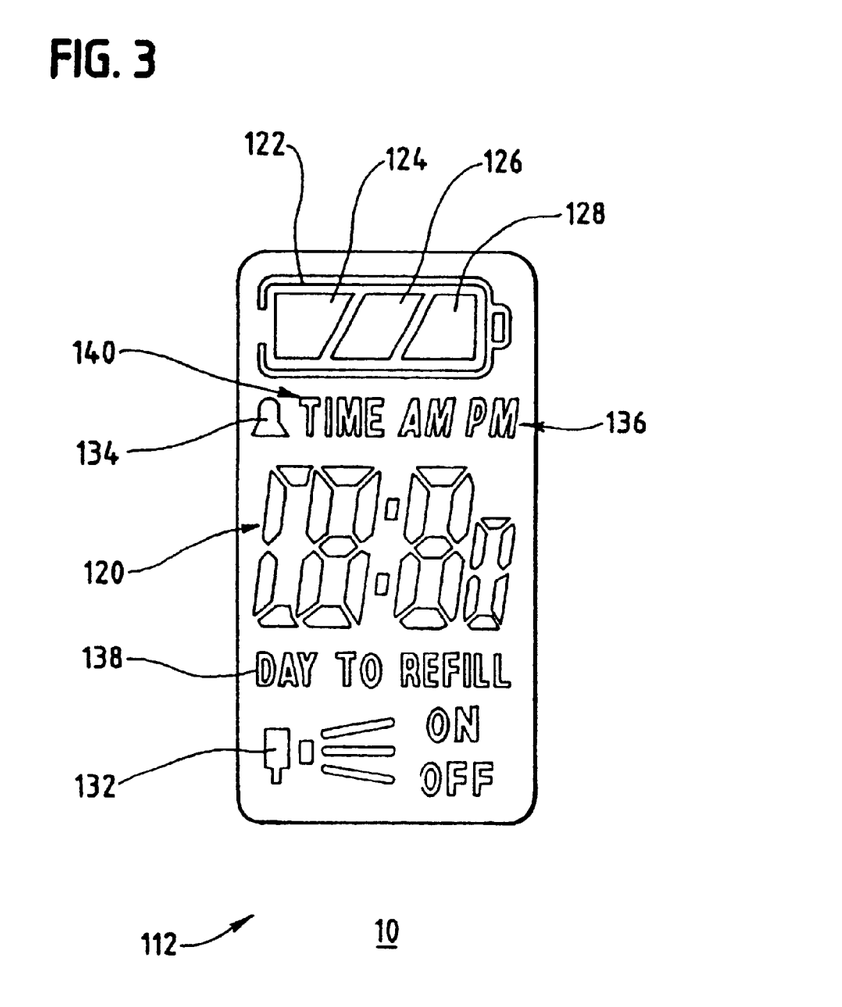
FIG. 3 is an enlarged view of the LCD display shown in FIG. 2.

FIG. 3 illustrates a specific embodiment of the LCD display 112 in greater detail. The LCD display 112 is preferably a three by thirty-four segment LCD having a numerical display 120 and other graphical icons, as will be described hereinafter. The LCD display 112 includes a three segment LCD graphical display 122 that appears in the shape of a battery having three separate portions formed by a first segment 124, a second segment 126, and a third segment 128. The three segment graphical display 122 provides the user with an indication of remaining battery power. The LCD display 112 further includes graphical icons, such as a SPRAY (PUMP) on/off indicator 132 that indicates whether spray (pump) adjustments are currently being accessed, a tone icon 134 indicating that generation of audible tones or other audio indicators is enabled, an AM/PM indicator 136, a "DAYS TO REFILL" indicator 138, and a TIME indicator 140 for setting time (FIG. 3). The DAYS TO REFILL indicator 138, when enabled, indicates that the number represented by the numerical display 120 is the number of days left until the container 18 (FIG. 1) is refilled or replaced.

A three-position slide switch 142 (FIG. 2) is provided under the control panel 102. The slide switch 142 is labeled as "A" in FIG. 2. The slide switch 142 controls the generation of tones, depending whether the switch is in an OFF position 150, a QUIET-ON position 152, or an AUDIO-ON position 154, as will be described in greater detail hereinafter.

In operation, the dispensing device 10 of the illustrated embodiment functions as follows. Upon initial activation by turning on the device via on/off switch 170, or after the batteries have been installed or replaced, the reset switch 104 is briefly depressed. The reset switch 104 is a pushbutton type switch that causes the electronics of the dispensing device 10 to be reset. The reset switch 104 is also briefly depressed when the container 18 is replaced to permit recalculation of the time remaining until refill, as will be described hereinafter.

The mode switch 106, the settings switch 108, and the enter switch 110 control the function of the dispensing device 10. A first depression of the mode switch 106 causes the dispensing device 10 to enter mode 1, a second depression of the mode switch causes the dispensing device to enter mode 2, a third depression of the mode switch causes the dispensing device to enter mode 3, and a fourth depression of the mode switch causes the dispensing device to enter mode 4. While in each mode, depression of the settings switch 108 modifies the particular option(s) available in that mode. Depression of the enter switch 110 selects and programs the available option presented to the user. If within a particular mode, an option is not entered within, for example, two minutes, mode 1 is automatically entered as a default mode and a particular mode option is automatically selected. Preferably, a short tone of about 0.5 seconds in length accompanies the user's depression of the mode switch 106 to provide user feedback. The short tone is also produced when the two minute time period elapses and mode 1 is entered by default.

Mode 1 determines the service day or the number of days between refills (i.e., the dispensing time frame that the dispensing device is to operate before refill of the aerosol is necessary). The service day or dispensing time can be selected from predetermined values, e.g., thirty (30) days, sixty (60) days, and ninety (90) days, where 30 days is defined to be the default value or factory programmed value. Alternatively, the user can enter a value for the service day. In either case, the dispensing device adjusts the dispensing time interval to accommodate a specific service day.

After the dispensing level in mode 1 has been selected, mode 2 is automatically entered and the user may make further choices. In mode 2, the actual time of day is entered. The settings switch 108 is used to increase the time displayed on the numerical display 120 in conjunction with the AM/PM indicator 136. When the correct time is displayed, the user depresses the enter switch 110 to program the dispensing device 10 with the correct time of day. Preferably, the time of day is advanced by ten-minute increments each time the settings switch 108 is depressed, but other increments may also be workable in this mode. After the correct time of day in mode 2 has been entered, mode 3 is automatically entered and the user may make further choices.

Mode 3 permits the user to select a "twelve hour on/off" option or a "twenty-four hour" option. In the illustrated embodiment, if the twelve-hour on/off option is selected, the dispensing device 10 will dispense material for a selected period of twelve hours during each twenty four-hour period. This is essentially a "day-time/night-time" option where the dispensing device 10 is programmed to dispense material, for example, during the day or night, respectively, but is governed solely by the time rather than the amount of light present. This option is typically selected to program fragrance "on" during the period when workers are present. Of course, this could occur during the day or at night, but workers are typically present during the daytime. The twelve-hour on/off option is identified by displaying the number "12" on the numerical display 120. The user then depresses the enter switch 110 to select this option. In the illustrated embodiment, if the twelve-hour on/off option is selected, the start time for dispensing is additionally selected. The user then enters the time at which to begin the twelve-hour dispensing period. For example, the user may enter 7:00 p.m. to begin the twelve-hour cycle. However, any time may be entered. Selection of the 12-hour on/off option in mode 3 essentially doubles the time between refilling the container 18 relative to the twenty-four hour option. Although the present invention is discussed in terms of a 12-hour or a 24 -hour option, in the alternative, the user can enter any value between 1 and 24 for the number of working hours/day during which the dispensing device 10 would be active.

If the twenty-four hour option is selected, the dispensing device 10 dispenses material throughout the entire twenty-four hour period according to the 30/60/90 option selected in mode 1. The twenty-four hour option is identified by displaying the number "24" on the numerical display 120. The twenty-four hour option represents the default condition. After the user has entered the twelve-hour or twenty-four hour option of mode 3, mode 4 is automatically entered and the user may make further choices.

In mode 4 of the illustrated embodiment, zero, one, or two days may be "skipped" each week so that dispensing is inhibited during selected days. This is essentially a "weekend" option where the user would typically inhibit dispensing during the weekend. However, any days of the week may be selected, and any number of days may be selected. When no days (zero days) are designated to be skipped, the option is referred to as the seven-day option because the dispensing device 10 operates seven days per week. When one day is designated to be skipped, the option is referred to as the six-day option. Similarly, when two days are designated to be skipped, the option is referred to as the five-day option. While in mode 4, the user depresses the settings switch 108 to select the seven day, the six day, or the five day option and then depresses the enter switch 110 to program that option. If anything other than the seven-day option is selected, the user will then select the particular day(s) of the week during which dispensing is inhibited. The day(s) of the week to be skipped are displayed on the numerical display 120 as "MO, TU, WE, TH, FR, SA, and SU," respectively. The day(s) selected to be skipped is then selected by depressing the enter switch 110. The seven-day option where no dispensing is inhibited represents the default condition.

In practice, the user selects the seven-day option simply by not selecting a day to be skipped. The six-day option is activated by the user's selection of a single day to be skipped, and the five-day option is activated by the user's selection of a second day to be skipped, etc.

The user may also review all of the selected options by depressing the mode switch 106 repeatedly without making selections. Selected options will not be changed unless the user depresses the settings switch 108 to change the option and subsequently depresses the enter switch 110 to program the selected option. As mentioned previously, if the user fails to depress the enter switch 110, after a delay of about two minutes the displayed selection is automatically programmed. Accordingly, the user may review all of the selected options previously entered or may review the default settings currently programmed. Optionally, a short tone of about 0.5 seconds in length accompanies the user's depression of the enter switch 110 to provide user feedback that the selected option has been programmed.

Figure 4A:
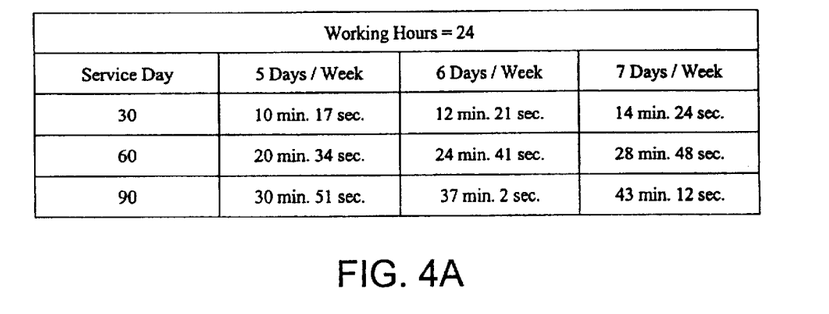
FIGS. 4A & B is table illustrating the various possibilities for the intervals between pulses when various options are selected.
Figure 4B:
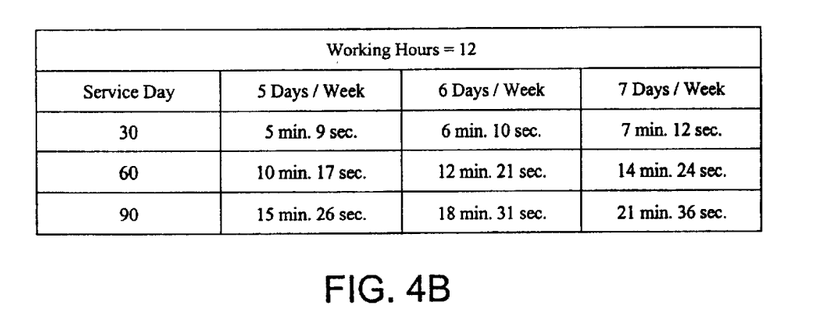

Based on the service day, the number of working hours/day and the working days, the control means sets the dispensing interval to a predetermined time period. FIG. 4 provides an indication of the various possibilities for dispensing intervals when the various options of mode 1, mode 3, and mode 4 are selected. In particular, FIG. 4 provides various dispensing intervals for service days or 30, 60, and 90, working hours/day of 12 and 24, and based on a workweek of 5-days, 6-days, and 7-days. As shown in FIG. 4, if the dispensing device is set for 7 days a week of 24 hour operation, the dispensing interval is initially set to 14 min. 24 sec. for 30 days to refill, 28 min. 48 sec. for 60 days to refill, or 43 min. 12 sec. for 90 days to refill. This dispensing interval is adjusted if the user chooses to have the dispensing device operate for 12 hours (half a day) instead of 24 hours (full day). If the user chooses to have the dispensing device operate for five or six days of the week instead of 7 days or operation, the dispensing interval is then decremented by two days or one day, respectively. Hence, as the user selects the operational limits, the control means automatically adjusts the dispensing interval to the known volume of the aerosol can, i.e., a full 3000 sprays to be completely dispensed over the selected number of days between refills. Of course, dispensing frequencies other that those provided may also be satisfactory. Specifically, the dispensing interval can be calculated using the following formula:

$$\text{Dispensing Interval} = \frac{86400 \text{ sec./day} * (\text{\# working days/wk}) * (\text{\# working hrs/day}) * (\text{dispensing time})}{3000 \text{ dispersements} * 7 \text{ days/wk} * 24 \text{ hrs/day}}$$

The 30/60/90 options of mode 1, the twelve hour/twenty-four option of mode 3, and the seven day/six day/five day option of mode 4 provide many different levels or frequencies of dispensing and hence, significantly affects the time between refills of the container 18. The indication of the days remaining to refill the container 18 is displayed on the numerical display 120 and represents a significant feature of the dispensing device 10.

Known dispensing devices do not allow the user to select the number of days between refills. Typically, known devices simply inform the user when the container is empty. Providing a selection of the number of days until a refill, i.e., the service day, is a significant feature and permits the user to timely schedule maintenance of the dispensing device 10 rather than estimating when the container 18 will need replacement or waiting until the container is empty. Timely scheduling of service calls is cost-effective and reduces labor costs associated with servicing the dispensing device 10. Such timely scheduling also insures uninterrupted operation. For example, a service call may be scheduled on a regular basis in 30-day cycles to insure timely servicing and uninterrupted operation of the dispensing device 10. This results in increased convenience for both on-site service and off-site service contractors.

Note that the above-described LCD display 112 and the operation of the control panel 102 with its various modes and options is not limited to a dispensing device 10 using a pressurized aerosol container 18. The dispensing device 10 may include, for example, a liquid pump container, a liquid drip container, or other suitable container.

Figure 5A:
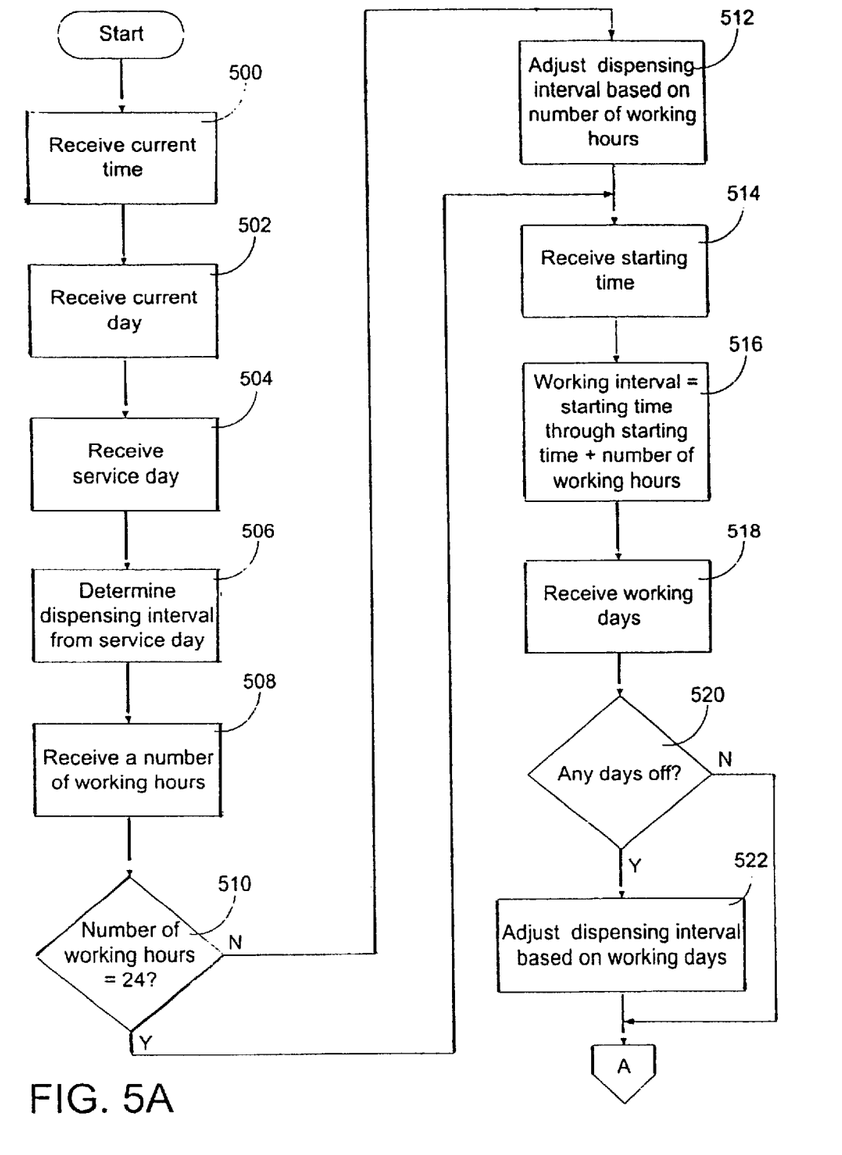
FIGS. 5A–5B depicts a flow chart of the steps performed by the dispensing apparatus of FIG. 1.
Figure 5B:
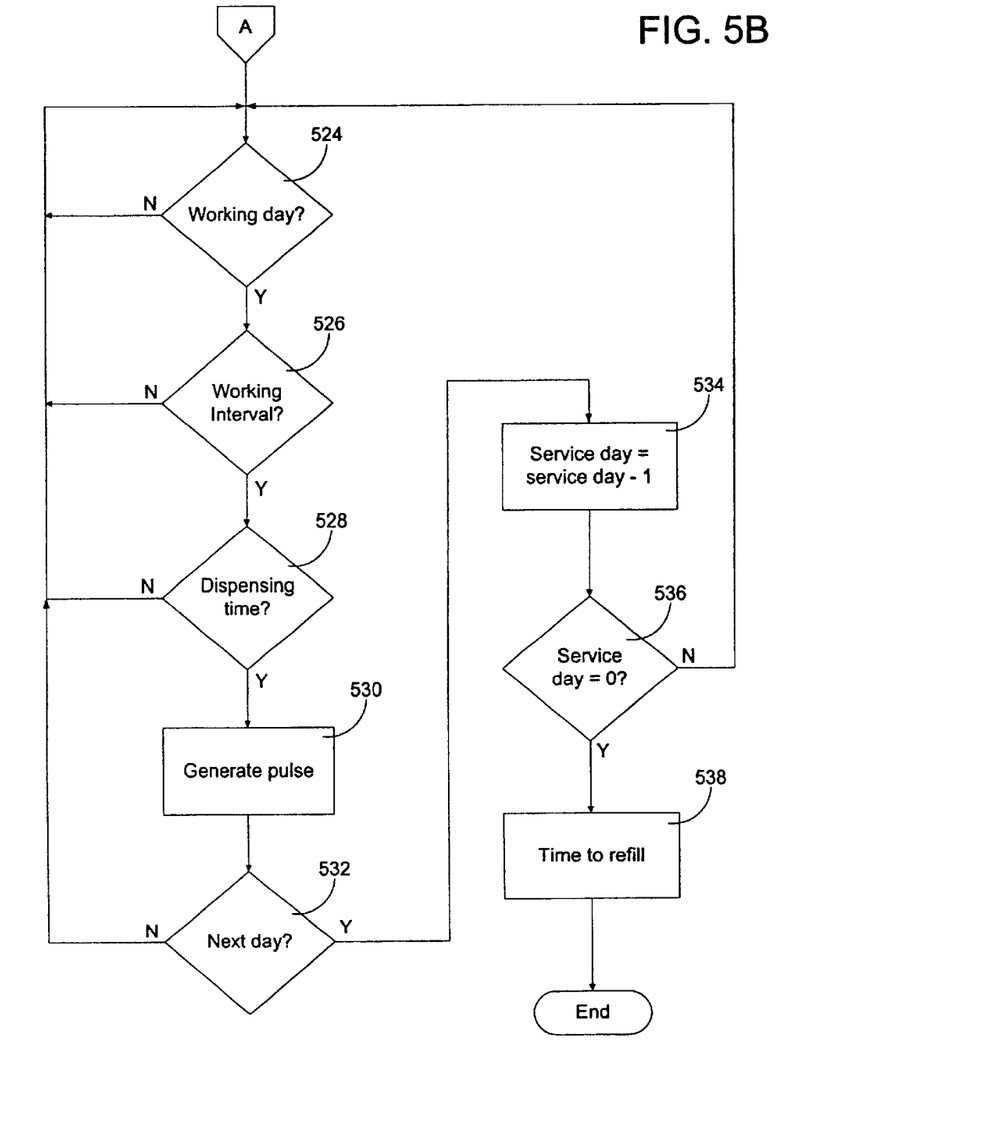

FIGS. 5A–B depict a flow diagram illustrating the overall system and method for programmably dispensing material, in accordance with the present invention. Initially, the dispensing device receives the current time and current day from the user. (Steps 500, 502). The dispensing device then receives the service day, i.e., 30-days, 60 days or 90 days. (Step 504). The dispensing interval is determined from the service day (step 506). The dispensing device then receives a number of working hours/day. (Step 508). If the number of working hours/day is 24, the dispensing interval is not adjusted; however, if the user chooses a 12-hour day, the dispensing interval is adjusted to accommodate the 12-hour day. (Steps 510, 512) The user enters the starting time, and the working interval is determined to run from the starting time through the starting time+the number of working hours/day. (Steps 514, 516). The user then enters the working days, and if any of the days are designated as not active, the dispensing interval is adjusted to account for the inactive days. (Steps 518, 520, 522).

The process continues in FIG. 5B, where the dispensing device determines whether the current time falls on a working day, during a working interval and at a dispensing time. (Steps 524, 526, 528). If so, the dispensing device generates a pulse. (Step 530). For each successive day, the service day is decremented, and after it reaches zero, the dispensing device provides a notice to the user that it is time to refill the dispensing device. (Steps 532, 534, 536, 538).

Figure 6:
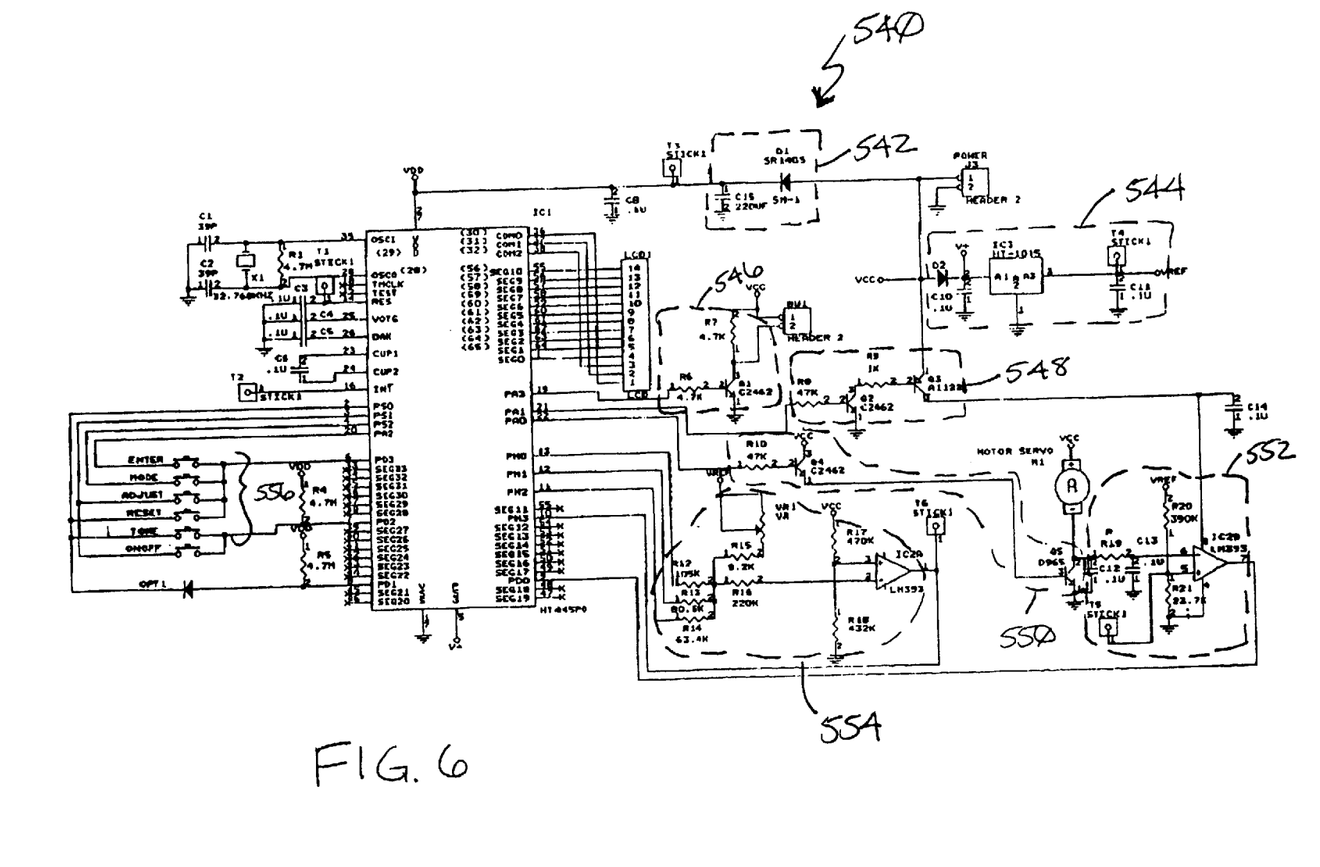
FIG. 6 is a schematic diagram for an embodiment of electronic circuitry of the device of FIG. 1.

Referring now to FIG. 6, there is shown a schematic diagram for a specific embodiment of electronic circuitry for the illustrated embodiment of the dispensing device 10 (FIG. 1). The schematic diagram of FIG. 4 illustrates a circuit 540 that controls all of the functions of the dispensing device 10. The microprocessor IC1 performs all control and display functions and operates the dispensing device 10 according to preprogrammed instructions. The microprocessor IC1 may be, for example, a four-bit microcomputer model HT445PR provided by Holtek, Inc. However, any suitable microcomputer or controller capable of controlling LCDs (liquid crystal display) and having input and output port capability may be used.

A diode D1 and a capacitor C15 form a voltage regulator circuit 542 to provide a stable voltage source for microprocessor IC1. The diode D2, capacitors C10, C11 and voltage regulator IC3 form a 1.5-volt constant voltage source 544 for voltage comparator IC2. The resistors R6 and R7 and transistor Q1 form a speaker drive 546 for tone feature. The resistors R8 and R9, and transistors Q2 and Q3 form a switch circuit 548 to control the power supply to voltage comparator IC2 for power savings purposes. The resistor R10, and transistors Q4 and Q5 form a motor driver circuit 550 to drive the motor M1. The capacitors C12 and C13, resistors R19, R20 and R21 and operational amplifier IC2B form a motor stall detecting circuit 552. When the motor M1 is at a stall condition, the operational amplifier IC2B pin 6 input voltage will be higher than pin 5 reference voltage, and the output pin 7 will change to a low state to stop the motor driver signal from reaching microprocessor IC1. The variable resistor VR1, resistors R12–R18 and operational amplifier IC2A form a battery voltage detecting and battery icon display control circuit 554. The battery voltage is divided by resistors R17 and R18 for pin 3 of operational amplifier IC2A, which is then compared with the pin 2 voltage. The resistors R12, R13 and R14 are switched to ground sequentially via microprocessor IC1 to provide a different reference voltage for pin 2 for 3 bar icon display. The OPTI diode is an option for a 9000 pump bottle. The capacitors C1 and C2, resistor R1, crystal X1 and OSCI and OSCO form an oscillator circuit for microprocessor IC1 for system timing. The six push button switches 556 are for system settings.

While various embodiments of the application have been described, it will be apparent to those of ordinary skill in the art that many more embodiments and implementations are possible that are within the scope of this invention. Accordingly, the invention is not to be restricted except in light of the attached claims and their equivalents.

What is claimed is:

1. An apparatus for dispensing material from a container, comprising:
    a valve connected to the container whereby the valve allows the material to escape from the container;
    a motor connected to the valve for actuating the valve; and
    a controller in signal communication with the motor, wherein said controller performs the steps of:
        receiving a dispensing time;
        receiving a working interval;
        receiving a plurality of working days; and
        controlling and activating the motor during the dispensing time, during the working interval and on one of the plurality of working days.

2. The apparatus of claim 1, wherein the dispensing time comprises one of the group consisting of 30 days, 60 days, and 90 days.

3. The apparatus of claim 1, wherein said controller further performs the steps of:
    receiving a current time; and
    receiving a start time, wherein the motor is controlled and activated when the current time equals the start time.

4. The apparatus of claim 3, wherein the step of receiving the working interval comprises the step of receiving a number of working hours/day, wherein the working interval starts when the current time equals the starting time and the working interval ends when the current time equals the starting time plus the number of working hours/day.

5. The apparatus of claim 4, wherein the number of working hours/day comprises one of the group consisting of 12 hours and 24 hours.

6. The apparatus of claim 1, wherein the one of the plurality of working days comprises one of the group consisting of Monday, Tuesday, Wednesday, Thursday, Friday, Saturday, and Sunday.

7. An apparatus for dispensing material from a container, comprising:
    a valve connected to the container whereby the valve allows the material to escape from the container;
    a motor connected to the valve for actuating the valve; and
    a controller in signal communication with the motor, wherein said controller performs the steps of:
        receiving a dispensing time;
        determining a dispensing interval based on the dispensing time; and
        controlling and activating the motor at a frequency inversely proportional to the dispensing interval.

8. The apparatus of claim 7, wherein the controller further performs the step of receiving a number of working hours/day, wherein the dispensing interval is inversely proportional to the number of working hours/day.

9. The apparatus of claim 8, wherein the number of working hours/day comprises one of the group consisting of 12 hours and 24 hours.

10. The apparatus of claim 7, wherein the controller further performs the step of determining a number of working days, wherein the dispensing interval is inversely proportional to the number of working days.

11. The apparatus of claim 10, wherein the step of determining the number of working days comprises the steps of:
    receiving a plurality of working days; and
    counting the number of working days.

12. The apparatus of claim 7, wherein the dispensing time comprises one of the group consisting of 30 days, 60 days, and 90 days.

13. The apparatus of claim 7, wherein the controller further performs the steps of:
    receiving a current time; and
    receiving a start time, wherein the material is dispensed from the container when the current time equals the start time.

14. An apparatus for dispensing material from a container, comprising:
    a valve connected to the container whereby the valve allows the material to escape from the container;
    a motor connected to the valve for actuating the valve; and
    a controller in signal communication with the motor, wherein said controller performs the steps of:

receiving a dispensing time;

receiving a number of working hours/day;

determining a number of working days;

determining a dispensing interval based on the dispensing time, the number of working hours/day and the number of working days; and controlling and activating the motor at a frequency inversely proportional to the dispensing interval.

15. The apparatus of claim 14, wherein the dispensing time comprises one of the group consisting of 30 days, 60 days, and 90 days.

16. The apparatus of claim 14, wherein the controller further performs the steps of:

receiving a current time; and receiving a start time, wherein the material is dispensed from the container when the current time equals the start time.

17. The apparatus of claim 14, wherein the number of working hours/day comprises one of the group consisting of 12 hours and 24 hours.

18. The apparatus of claim 14, wherein the step of determining the number of working days comprises the steps of:

receiving a plurality of working days; and counting the number of working days.

19. The apparatus of claim 18, wherein the one of the plurality of working days comprises one of the group consisting of Monday, Tuesday, Wednesday, Thursday, Friday, Saturday, and Sunday.

20. A system for dispensing material from a container, comprising:

means for receiving a dispensing time;

means for receiving a working interval;

means for receiving a plurality of working days; and means for dispensing the material from the container during the dispensing time, during the working interval and on one of the plurality of working days.

21. A system for dispensing material from a container, comprising:

means for receiving a dispensing time;

means for determining a dispensing interval based on the dispensing time; and means for dispensing the material from the container at a frequency inversely proportional to the dispensing interval.

22. A system for dispensing material from a container, comprising:

means for receiving a dispensing time;

means for receiving a number of working hours/day;

means for determining a number of working days;

means for determining a dispensing interval based on the dispensing time, the number of working hours/day and the number of working days; and means for dispensing the material from the container at a frequency inversely proportional to the dispensing interval.

* * * * *